(12) United States Patent
Yanai et al.

(10) Patent No.: US 6,288,038 B1
(45) Date of Patent: Sep. 11, 2001

(54) DEPSIPEPTIDE DERIVATIVES BEARING PIPERAZINONE RINGS

(75) Inventors: Makoto Yanai; Masashi Suzuki; Norio Oshida; Koji Kawamura; Shigeru Hiramoto; Orie Yasuda; Nobuhiro Kinoshita; Akiko Shingai; Masako Takasu, all of Saitama-ken (JP)

(73) Assignee: Nisshin Seifun Group Inc., Tokyo (JP)

( * ) Notice: Subject to any disclaimer, the term of this patent is extended or adjusted under 35 U.S.C. 154(b) by 0 days.

(21) Appl. No.: 09/509,132
(22) PCT Filed: Aug. 4, 1999
(86) PCT No.: PCT/JP99/04205
   § 371 Date: Apr. 3, 2000
   § 102(e) Date: Apr. 3, 2000
(87) PCT Pub. No.: WO00/08047
   PCT Pub. Date: Feb. 17, 2000

(30) Foreign Application Priority Data

Aug. 4, 1998 (JP) ................................... 10-220398

(51) Int. Cl.$^7$ ......................... A61K 31/50; A61K 38/06; C07D 241/08; C07D 5/062; C07D 5/083
(52) U.S. Cl. ............................. 514/18; 514/19; 514/252; 514/255; 530/323; 530/331; 544/357; 544/384
(58) Field of Search .................... 514/2, 18, 19, 514/20, 252, 255; 530/300, 323, 330, 331, 345; 544/357, 384

(56) References Cited

U.S. PATENT DOCUMENTS 4,593,098 * 6/1986 Moon .................................. 544/373

FOREIGN PATENT DOCUMENTS

| 927723 | 7/1999 | (EP) . |
| 931792 | 7/1999 | (EP) . |
| 11-263797 | 9/1999 | (JP) . |
| 97/49722 | 12/1997 | (WO) . |
| 97/49724 | 12/1997 | (WO) . |

OTHER PUBLICATIONS

Pohlmann et al. Synthesis and conformational analysis of two 2–oxopiperazine–containing tetrapeptide analogues. J. Peptide Research. vol. 51, pp. 116–120 (1998).*
"Increased Clearance of Plasma Cholesterol After Injection of Apolipoprotein E Into Watanabe Heritable Hyperlipidemic Rabbits", by Yamada et al., Proc. Natl. Acad. Sci. USA, vol. 86, Jan. 1989, pp. 665–669.
"Plasma Lipoprotein Metabolism in Transgenic Mice Overexpressing Apolipoprotein E: Accelerated Clearance of Lipoproteins Containing Apolipoprotein B", by Shimano et al., Journal of Clinical Investigation, vol. 90, 1992, pp. 2084–2091.
"Expression of Apolipoprotein E During Nerve Degeneration and Regeneration", by Ignatius et al., Proc. Natl. Acad. Sci. USA, vol. 83, Feb. 1986, pp. 1125–1129.
"Specific Neurochemical Derangements of Brain Projecting Neurons in Apolipoprotein E–Deficient Mice", by Chapman et al., Journal of Neurochemistry, vol. 7, No. 2, 1998, pp. 708–717.
"Neurodegeneration and Cognitive Impairment in apoE–Deficient Mice is Ameliorated by Infusion of Recombinant apoE", by Masliah et al., Brain Research, vol. 751, 1997, pp. 307–314.

* cited by examiner

Primary Examiner—Jeffrey E. Russel
(74) Attorney, Agent, or Firm—McDermott, Will & Emery

(57) ABSTRACT

The present invention provides a new depsipeptide derivative having a piperazinone ring within the molecule which is represented by formula (1)

$$O-CO-CH(R_2)-X_1-CH(R_3)-A \quad (1)$$
$$R_1-CH-CH_2-B$$

wherein $X_1$ represents $N(R_4)-CO$, $N(R_5)-CH_2$, $CH_2-CO$, $CH_2-CH_2$, $CH=CH$, $CH_2-CH(OH)$ or $CH(OH)-CH(OH)$, $R_1$ represents a $C_5-C_{20}$ alkyl group or a $C_5-C_{15}$ alkoxy $C_1-C_4$ alkyl group, $R_2-R_5$ represent a hydrogen atom or a $C_1-C_6$ alkyl group, and A represents a group of formula (2), (3) or (4)

(2) [structure with $R_8$, $R_6$, $R_7$]

(3) [structure with $R_{10}$, $R_9$]

$$-X_2-CH(R_{11})-X_3-CH(R_{12})-NH-R_{13}. \quad (4)$$

The depsipeptide derivative has a function of accelerating the production of apolipoprotein E and is useful as an agent for the treatment of neurologic injury, an agent for the treatment of dementia and an antihyperlipidemic agent.

8 Claims, No Drawings

DEPSIPEPTIDE DERIVATIVES BEARING PIPERAZINONE RINGS

TECHNICAL FIELD

This invention relates to new depsipeptide derivatives having a piperazinone ring within the molecule and medicines comprising the same as an active ingredient. The depsipeptide derivatives containing a piperazinone ring of the present invention have a function of accelerating the production of apolipoprotein E, and also they are useful as antihyperlipidemic agents, agents for the treatment of neurologic injury and agents for the treatment of dementia.

BACKGROUND ART

It has recently been reported that a remarkable reduction in a plasma cholesterol level is observed when apolipoprotein E is administered intravenously to WHHL rabbit which is a model animal for human familial hypercholesterolemia homozygote (see Yamada et al., Proc. Natl. Acad. Sci. U.S.A., Vol. 86, pp. 665–669, (1989)), and also that plasma cholesterol and triglyceride are remarkably decreased by transducing a gene of apolipoprotein E into a mouse liver and expressing apolipoprotein E in a large quantity (see Shimano, H. et al., Journal of Clinical Investigation, Vol. 90, pp. 2084–2091, (1992)).

As reported in these references, an increase in plasma apolipoprotein E level has been extremely effective as a method for the treatment of hyperlipemia, especially familial hypercholesterolemia homozygote which has been considered to be difficult to treat with prior drugs.

Activators of cerebral circulation and metabolism have been mainly used as an agent for the treatment of senile dementia, but they do not exhibit any improved effect on a disintegration of the central nervous system which is considered to be the cause of senile dementia. On the other hand, it has been reported that apolipoprotein E may be expressed at a high level in the site of nervous system which is injured and being recovered (for example, see M. J. Ignatius et al., Proc. Natl. Acad. Sci. U.S.A., 83, 1125, (1986)), which suggests that apolipoprotein E will play an important role in repairing the nervous system.

Recently, comparative studies of the neuronal metabolism and function in apolipoprotein E-deficient mice and control mice have revealed that a selective degeneration of the central nervous system is observed in apolipoprotin E-deficient mice and this is remarkably similar to the selective degeneration of the neuronal system observed in neurodegenerative diseases such as Alzheimer's disease and Parkinson's disease (see S. Chapman and D. M. Michaelson, J. Neurochem., vol. 7, No. 2, pp. 708–714, (1998)). Thus apolipoprotein E is considered to play a role essential for the maintenance of central nervous system.

It has been reported that an administration of apolipoprotein E to apolipoprotein E-deficient mice provides a remarkable improvement in the learning capacity and restoration of neuronal structure, which suggests that apolipoprotein E plays a neurotrophic effect to maintain and restore the nervous systems in vivo, and that it is useful in the treatment of human neurodegenerative diseases (see E. Masliah et al., Brain Res. 751, pp. 307–314, (1997)).

In view of the foregoing facts, it has been desired to elucidate drugs of increasing a plasma apolipoprotein E level for a method of treating hyperlipemia, especially familial hypercholesterolemia homozygote which has been considered to be difficult to treat with prior drugs.

Further, it has been desired to elucidate drugs which promote the repair and growth of the nervous system and inhibit the disintegration of the central nervous system, for an agent for the treatment of a new type of senile dementia. This may be accomplished by promoting the production of apolipoprotein E.

Under such circumstances, the present inventors have studied in an effort to provide the agents for promoting the production of apolipoprotein E, and found that depsipeptide derivatives having a specific structure possess the above function.

DISCLOSURE OF THE INVENTION

The present invention relates to a depsipeptide derivative containing a piperazinone ring represented by formula (1)

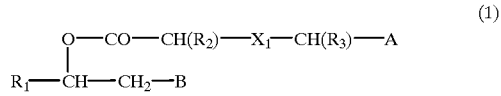

(1)

wherein $X_1$ represents $N(R_4)$—CO, $N(R_5)$—$CH_2$, $CH_2$—CO, $CH_2$—$CH_2$, CH=CH, $CH_2$—CH(OH) or CH(OH)—CH(OH), $R_1$ represents a $C_5$–$C_{20}$ alkyl group or a $C_5$–$C_{15}$ alkoxy $C_1$–$C_4$ alkyl group, $R_2$–$R_5$ represent a hydrogen atom or a $C_1$–$C_6$ alkyl group, A represents a group of formula (2), (3) or (4)

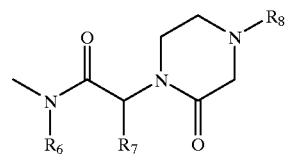

(2)

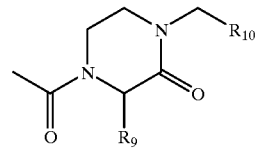

(3)

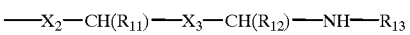

(4)

wherein $X_2$ and $X_3$ each independently represent $N(R_{14})$—CO, $N(R_{15})$—$CH_2$, $CH_2$—CO, $CH_2$—$CH_2$, CH=CH, $CH_2$—CH(OH) or CH(OH)—CH(OH), $R_6$, $R_{12}$, $R_{14}$ and $R_{15}$ represent a hydrogen atom or a $C_1$–$C_6$ alkyl group, $R_7$, $R_9$ and $R_{11}$ represent $(CH_2)_{m1}$—COOH wherein $m_1$ represents an integer of 1–3 or $(CH_2)_{n1}$—$CONH_2$ wherein $n_1$ represents 2 or 3, $R_8$ and $R_{13}$ represent a hydrogen atom or an amine-protecting group usually used in peptide chemistry, and $R_{10}$ represents a hydrogen atom, a $C_1$–$C_6$ alkyl group, a carboxyl group or a $C_1$–$C_6$ alkoxycarbonyl group, and B represents a carboxyl group, a $C_1$–$C_6$ alkoxycarbonyl group or a group of formula (5)

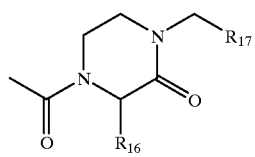

(5)

wherein $R_{16}$ represents $(CH_2)_{m2}$—COOH wherein $m_2$ represents an integer of 1–3 or $(CH_2)_{n2}$—$CONH_2$ wherein $n_2$ represents 2 or 3, and $R_{17}$ represents a hydrogen atom, a $C_1$–$C_6$ alkyl group, a carboxyl group or a $C_1$–$C_6$ alkoxycarbonyl group, provided that the carboxyl group in the above-mentioned A and B may be protected by an protecting group usually used in peptide chemistry, and that when A is a group represented by formula (4), B is a group represented by formula (5), or a pharmacologically acceptable salt thereof.

In the preferred embodiment, the present invention relates to a depsipeptide derivative containing a piperazinone ring represented by formula (1')

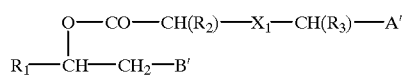

(1')

wherein $X_1$ represents $N(R_4)$—CO, $N(R_5)$—$CH_2$, $CH_2$—CO, $CH_2$—$CH_2$, CH=CH, $CH_2$—CH(OH) or CH(OH)—CH(OH), $R_1$ represents a $C_5$–$C_{20}$ alkyl group or a $C_5$–$C_{15}$ alkoxy $C_1$–$C_4$ alkyl group, $R_2$–$R_5$ represent a hydrogen atom or a $C_1$–$C_6$ alkyl group, A' represents a group of formula (2)

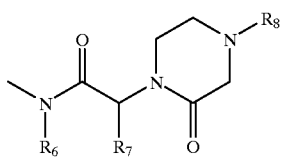

(2)

wherein $R_6$ represents a hydrogen atom or a $C_1$–$C_6$ alkyl group, $R_7$ represents $(CH_2)_{m1}$—COOH wherein $m_1$ represents an integer of 1–3 or $(CH_2)_{n1}$—$CONH_2$ wherein $n_1$ represents 2 or 3, and $R_8$ represents a hydrogen atom or an amine-protecting group usually used in peptide chemistry, and B' represents a carboxyl group or a $C_1$–$C_6$ alkoxycarbonyl group, provided that the carboxyl group in the above-mentioned A' and B' may be protected by a protecting group usually used in peptide chemistry, or a pharmacologically acceptable salt thereof.

In another embodiments, the present invention relates to a depsipeptide derivative having a piperazinone ring represented by formula (1")

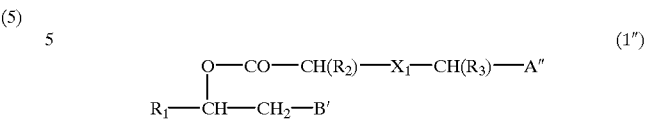

(1")

wherein $X_1$ represents $N(R_4)$—CO, $N(R_5)$—$CH_2$, $CH_2$—CO, $CH_2$—$CH_2$, CH=CH, $CH_2$—CH(OH) or CH(OH)—CH(OH), $R_1$ represents a $C_5$–$C_{20}$ alkyl group or a $C_5$–$C_{15}$ alkoxy $C_1$–$C_4$ alkyl group, $R_2$–$R_5$ represent a hydrogen atom or a $C_1$–$C_6$ alkyl group, A" represents a group of formula (3)

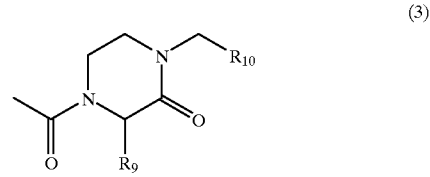

(3)

wherein $R_9$ represents $(CH_2)_{m1}$—COOH wherein $m_1$ represents an integer of 1–3 or $(CH_2)_{n1}$—$CONH_2$ wherein $n_1$ represents 2 or 3, and $R_{10}$ represents a hydrogen atom, a $C_1$–$C_6$ alkyl group, a carboxyl group or a $C_1$–$C_6$ alkoxycarbonyl group, and B' represents a carboxyl group or a $C_1$–$C_6$ alkoxycarbonyl group, provided that the carboxyl group in the above-mentioned A" and B' may be protected by an protecting group usually used 4 .0in peptide chemistry, or a pharmaceutically acceptable salt thereof.

In a depsipeptide derivative containing a piperazinone ring represented by formulae (1)–(1"), an alkyl group and an alkoxyl group are straight- or branched-chain, and a $C_5$–$C_{20}$ alkyl group include, for example, pentyl, isopentyl, t-pentyl, 1-methylbutyl, hexyl, isohexyl, heptyl, neopentyl, 1-methylheptyl, octyl, nonyl, decyl, undecyl, dodecyl, tridecyl, tetradecyl, pentadecyl, hexadecyl, heptadecyl, octadecyl, nonadecyl, icosyl and the like. A $C_1$–$C_6$ alkyl group include, for example, methyl, ethyl, n-propyl, isopropyl, n-butyl, isobutyl, t-butyl, n-pentyl, n-hexyl and the like, and a $C_1$–$C_6$ alkoxycarbonyl include, for example, methoxycarbonyl, ethoxycarbonyl, t-butoxycarbonyl and the like. A $C_5$–$C_{15}$ alkoxy $C_1$–$C_4$ alkyl group for $R_1$ is, for example, pentyloxymethyl, hexyloxymethyl, heptyloxymethyl, octyloxymethyl, nonyloxymethyl, decynyloxymethyl, undecynyloxymethyl, tridecynyloxymethyl, tetradecynyloxymethyl, pentadecynyloxymethyl, pentyloxyethyl, hexyloxyethyl, heptyloxyethyl, octyloxyethyl, nonyloxyethyl, decynyloxyethyl, undecynyloxyethyl, tridecynyloxyethyl, tetradecynyloxyethyl, pentadecynyloxyethyl, pentyloxypropyl, hexyloxypropyl, heptyloxypropyl, octyloxypropyl, nonyloxypropyl, decynyloxypropyl, undecynyloxypropyl, tridecynyloxypropyl, tetradecynyloxypropyl, pentadecynyloxypropyl, pentyloxybutyl, hexyloxybutyl, heptyloxybutyl, octyloxybutyl, nonyloxybutyl, decynyloxybutyl, undecynyloxybutyl, tridecynyloxybutyl, tetradecynyloxybutyl, pentadecynyloxybutyl and the like.

The protecting groups for an amine and a carboxyl group used in the depsipeptide derivatives containing a piperazinone ring represented by formula (1) of the invention are described in Nobuo Izumiya et al., "Fundamentals and Experiments for Peptide Synthesis" (Maruzen Co., Ltd., 1985).

The protecting groups for an amine include a t-butoxycarbonyl group (hereinafter referred to as "Boc"), a benzyloxycarbonyl group (hereinafter referred to as "Cbz"), a p-methoxybenzyloxycarbonyl group, a 9-fluorenylmethoxycarbonyl group (hereinafter referred to as "Fmoc"), a p-nitrobenzyloxycarbonyl group, an isobornyloxycarbonyl group, a p-biphenylisopropyloxycarbonyl group, a 3,5-dimethoxy-α,α-dimethylbenzylcarbonyl group, a methylsulfonyloxycarbonyl group, an isonicotinyloxycarbonyl group, a 2,2,2-trichloroethyloxycarbonyl group, a 2-(trimethylsilyl)ethoxycarbonyl group, a formyl group, a phthaloyl group, a dithiasuccinoyl group, a p-toluenesulfonyl group, a o-nitrophenylsulfenyl group, a 2-nitrophenylthio group, a 3-nitro-2-pyridinesulfenyl group, a diphenylphosphinyl group, a diphenylphosphinothioyl group, a dimethylphosphinothioyl group, a triphenylmethyl group, a 2-benzoyl-1-methylvinyl group and the like. Boc, Cbz, Fmoc and p-methoxybenzyloxycarbonyl group are preferable.

The protecting groups for the carboxyl group include esters such as benzyl ester (a benzyloxy group, hereinafter referred to as "OBzl"), tertiary butyl ester (a t-butoxy group, hereinafter referred to as "OtBu"), methyl ester, ethyl ester, phenacyl ester (phenacyloxy, hereinafter referred to as "OPac"), trichloroethyl ester, p-nitrobenzyl ester, diphenylmethyl ester, benzhydryl ester, p-methoxybenzyl ester, 4-picolyl ester, cyclohexyl ester and the like. OBzl, OtBu, OPac and the like are preferable.

In the depsipeptide derivatives containing a piperazinone ring represented by formulae (1') and (1"), B' is preferably a carboxyl group.

The invention also relates to a medicine comprising as an active ingredient a depsipeptide derivative containing a piperazinone ring represented by formula (1) and formulae (1')–(1") in the preferred embodiments or a pharmacologically acceptable salt thereof.

More particularly, the invention relates to an accelerator for the production of apolipoprotein E, more specifically, an agent for the treatment of neurologic injury, an agent for the treatment of dementia and an antihyperlipidemic agent, which comprise as an active ingredient a depsipeptide derivative containing a piperazinone ring represented by formula (1) and formulae (1')–(1") in the preferred embodiments or a pharmacologically acceptable salt thereof.

A depsipeptide derivative containing a piperazinone ring or a pharmacologically acceptable salt thereof of the invention can be prepared by using methods conventionally employed in the peptide synthesis, for example, a condensing agent method, an azide method, a chloride method, an acid anhydride method, a mixed acid anhydride method, an active ester method, a redox method, an enzyme method or the like as described in Nobuo Izumiya et al., "Fundamentals and Experiments for Peptide Synthesis" (Maruzen Co., Ltd., 1985).

The depsipeptide derivatives containing a piperazinone ring or the pharmacologically acceptable salts thereof of the invention can be prepared, for example, by protecting a carboxyl group in a 3-hydroxycarboxylic acid of the following formula

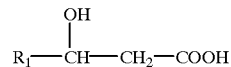

wherein $R_1$ has the same meaning as defined above, with a protecting group to form an ester, and condensing a hydroxyl group in the 3-hydroxycarboxylic acid with a carboxyl group in an aminocarboxylic acid or the like, of which an N-terminal or a C-terminal is protected, by a conventional method, and deprotecting the N-terminal or the C-terminal of the protecting group for the aminocarboxylic acid or the like, followed by condensing with an aminocarboxylic acid or the like having the desired piperazinone ring according to a conventional method for the peptide synthesis. If necessary, the protecting group of the carboxyl group of 3-hydroxycarboxylic acid may be deprotected, and further condensed with the piperazinone ring.

The depsipeptide derivatives can be also prepared by condensing a carboxyl group in the 3-hydroxycarboxylic acid with the piperazinone ring or a $C_1$–$C_6$ alcohol according to a conventional method, and condensing a hydroxyl group in the 3-hydroxycarboxylic acid with a carboxyl group in an aminocarboxylic acid or the like, of which an N-terminal or a C-terminal is protected, by a conventional method, and deprotecting the N-terminal or the C-terminal of the protecting group for the aminocarboxylic acid or the like, followed by condensing with an aminocarboxylic acid or the like having the desired piperazinone ring according to a conventional method for the peptide synthesis.

An alternative method, they can be prepared by preliminarily condensing an amino acid required previously with the above-mentioned aminocarboxylic acid, followed by linking it to the hydroxyl or carboxyl group in the 3-hydroxycarboxylic acid through an ester bond or an amide bond.

The protection of the carboxyl group in the 3-hydroxycarboxylic acid can be carried out by a methylesterification reaction wherein the carboxyl group is reacted with diazomethane in a solvent such as ether, methanol or the like under ice-cooling or at room temperature, or by a benzylesterification reaction wherein the carboxyl group is reacted with benzyl bromide in the presence of a basic substance such as triethylamine, in a solvent such as dimethylformamide (hereinafter referred to as "DMF"), dimethyl sulfoxide (hereinafter referred to as "DMSO") or the like at room temperature or under heating.

The condensation of an aminocarboxylic acid to the hydroxyl group in a compound having the protected carboxyl group may be carried out using as a condensing reagent N,N'-dicyclohexylcarbodiimide (hereinafter referred to as "DCC") or 1-ethyl-3-(3'-dimethylaminopropyl)carbodiimide hydrochloride, i.e., water-soluble carbodiimide (hereinafter referred to as "WSCI") in a solvent such as ether, acetone, chloroform, dichloromethane, ethyl acetate, DMF, tetrahydrofuran (hereinafter referred to as "THF"), acetonitrile, DMSO or the like under ice-cooling or at room temperature, preferably in the presence of a catalyst for acylation such as dimethylaminopyridine (hereinafter referred to as "DMAP").

Illustrative examples of 3-hydroxycarboxylic acids used as a starting material for the depsipeptide derivative containing a piperazinone ring can include 3-hydroxycaprylic acid, 3-hydroxypelargonic acid, 3-hydroxycapric acid, 3-hydroxylauric acid, 3-hydroxymyristic acid, 3hydroxypalmitic acid, 3-hydroxymargaric acid, 3-hydroxystearic acid, 4-octyloxy-3-hydroxybutyric acid, 4-nonyloxy-3-hydroxybutyric acid, 4-decyloxy-3-hydroxybutyric acid, 4-undecyloxy-3-hydroxybutyric acid, 4-dodecyloxy-3-hydroxybutyric acid, 4-tridecyloxy-3-hydroxybutyric acid and the like.

As the 3-hydroxycarboxylic acids, optically active R-isomers or S-isomers and racemates can be used, and R-isomers are preferably used when $R_1$ is a $C_5$–$C_{20}$ alkyl group, while S-isomers are preferably used when $R_1$ is a $C_5$–$C_{15}$ alkoxy $C_1$–$C_4$ alkyl group.

In preparing the depsipeptide derivatives containing a piperazinone ring of the above-mentioned formula (1) using a condensing agent, the agents can be used such as DCC, WSCI, O-(1H-benzotriazol-1-yl)-N,N,N',N'-tetramethyluronium tetrafluoroborate, benzotriazol-1-yl-oxy-tris(dimethylamino)phosphonium hexafluorophosphate, 3-(dimethoxyphosphoryloxy)-1,2,3-benzotriazine (hereinafter referred to as "DEPBT") or O-(7-azabenzotriazol-1-yl)-1,2,3 tetramethyluronium hexafluorophosphate (hereinafter referred to as "HATU") and the like. It is also preferable to simultaneously add the additives usually employed for preventing racemization, for example, N-hydroxysuccinimide, 1-hydroxybenzotriazole (hereinafter referred to as "HOBt"), N-hydroxy-5-norbornene-2,3-dicarbodiimide benzotriazole, 1-hydroxy-7-azabenzotriazole (hereinafter referred to as "HOAt") and the like.

Typical condensing agents used in the azide method include diphenylphosphoric azide and the like.

Before carrying out the condensation reaction, known conventional protecting means are preferably applied to the carboxyl group, amino group and the like not involved in said condensation reaction.

In this case, a variety of the above-mentioned protecting groups can be used in such protecting means.

In the elimination reaction of the protecting group in the process steps for the preparation of the depsipeptide derivative containing a piperazinone ring, it is required that the protecting group can be removed without giving any influence on the peptide bond. The elimination reaction may be appropriately selected, depending on the type of the protecting group used.

The solvents which may be used in the synthesis of each peptide include, for example, chloroform, dichloromethane, ethyl acetate, DMF, DMSO, pyridine, dioxane, THF, dimethoxyethane, acetonitrile or a mixture of these two or more solvents. This condensation reaction is carried out at a temperature ranging from about –20 to 50° C.

For the peptide synthesis, any of a liquid phase method and a solid phase method can be employed. Further, a column method or a batch method may be used.

The present depsipeptide derivatives containing a piperazinone ring thus prepared in the form of salts can be converted to the corresponding free forms. The depsipeptide derivatives thus prepared in the free forms can be converted to the corresponding pharmacologically acceptable salts. When the depsipeptide derivatives are in the form of the acidic compounds due to the presence of a carboxyl group therein, the corresponding acidic compounds can be formed with pharmacologically acceptable inorganic or organic bases into the salts thereof such as sodium, potassium, calcium and ammonium salts. When the depsipeptide derivatives are in the form of the basic compounds due to the presence of an amino group therein, the corresponding basic compounds can be formed with pharmacologically acceptable inorganic or organic acids into the inorganic salts such as hydrochlorides, hydrobromides, sulfates and phosphates, or the organic salts such as acetates, succinates, oxalates, malates and tartarates.

The depsipeptide derivatives containing a piperazinone ring represented by the formula (1) of the invention can be prepared by a variety of methods, illustrative examples of which are shown in the following Reaction Schemes 1–4.

In the reaction procedure according to Reaction Scheme 1, p-methoxycinnamic aldehyde and L-aspartic acid α-benzyl β-t-butyl ester were reacted to form Intermediate 1, Fmoc glycine was reacted with Intermediate 1 to form Intermediate 2, which was then ozonized to form Intermediate 3, and Intermediate 3 was catalytic-reduced to form Intermediate 4.

The carboxyl group of 3-hydroxycarboxylic acid, e.g., 3-hydroxymyristic acid was protected with phenacyl bromide to give, Intermediate 5, and the amino group of 5-amino-3-pentenoic acid was protected with Fmoc-Cl to give Intermediate 6. Intermediate 5 and Intermediate 6 were reacted to give Intermediate 7 and then the protecting group Fmoc for the amino group of Intermediate 7 was deprotected to give Intermediate 8.

Intermediate 4 and Intermediate 8 as prepared above were reacted to give the aimed Compound 1. Subsequently, the protecting groups of Compound 1 were removed in turn to give Compounds 2 and 3, respectively.

Reaction Scheme 1

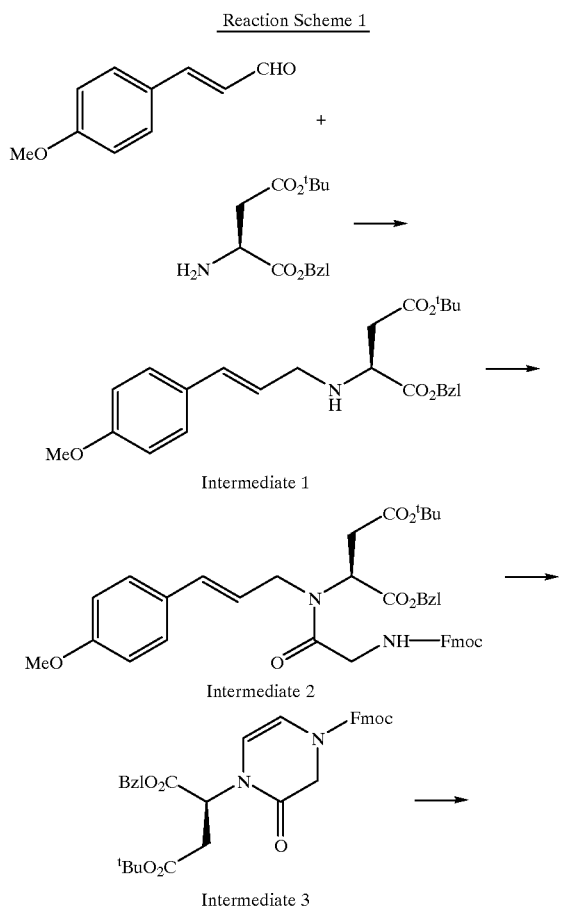

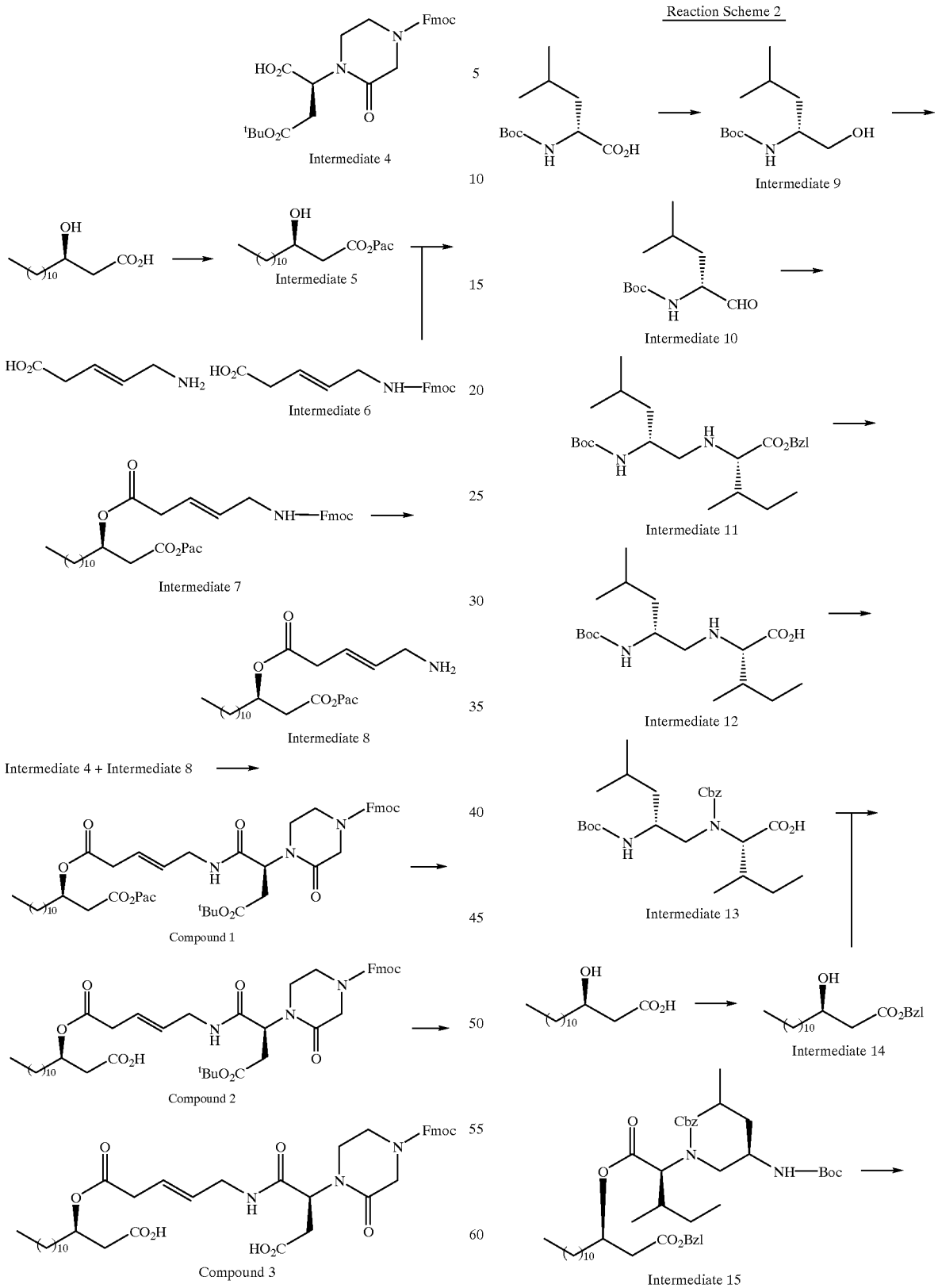

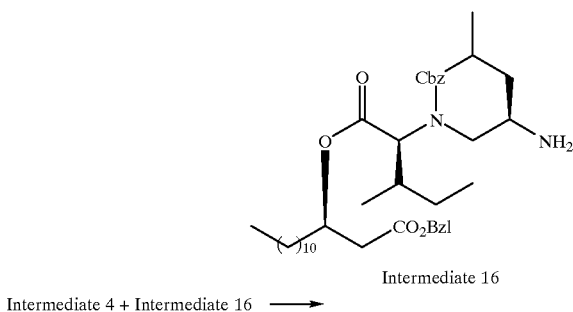

Intermediate 16

Intermediate 4 + Intermediate 16 ⟶

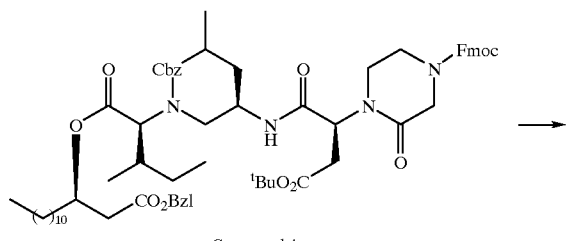

Compound 4

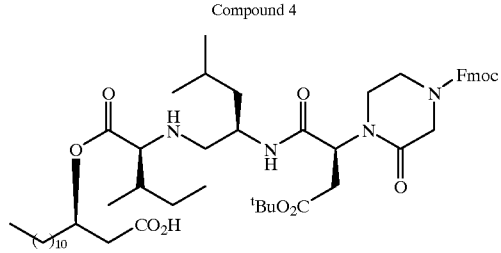

Compound 5

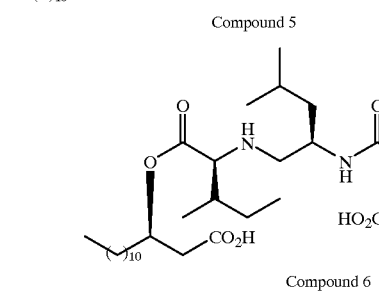

Compound 6

In the reaction procedure according to Reaction Scheme 2, Boc-D-leucine was reduced with sodium borohydride to give Intermediate 9, which was then oxidized to convert an alcohol in Intermediate 9 into an aldehyde, thus giving Intermediate 10. Intermediate 10 was reacted with isoleucine having the protected carboxyl group to give Intermediate 11. The carboxyl group of Intermediate 11 was deprotected to give Intermediate 12, and the amino group of Intermediate 12 was protected to give Intermediate 13.

The carboxyl group of 3-hydroxymyristic acid was protected to give Intermediate 14, which was then esterified with Intermediate 13 to give Intermediate 15. The protecting group for the amino group of Intermediate 15 was deprotected to give Intermediate 16. Intermediate 16 was reacted with Intermediate 4 to give Compound 4, and the protecting groups of Compound 4 were removed in turn to give Compounds 5 and 6, respectively.

In the reaction procedure according to Reaction Scheme 3, p-methoxycinnamic aldehyde and L-glycine tert-butyl ester were reacted to give Intermediate 17, which was then reacted with Fmoc-D-aspartic acid P-tert-butyl ester to give Intermediate 18. Intermediate 18 was reacted with ozone to break the double bond, which was then subjected to cyclization to give Intermediate 19. The protecting group for the amino group of Intermediate 19 was deprotected to give Intermediate 20.

One of the carboxyl groups in 2-buten-1,4-dicarboxylic dicarboxylic acid was protected to give Intermediate 21, and the carboxyl group of 3-hydroxymyristic acid was protected to give Intermediate 22. Intermediate 21 and Intermediate 22 were reacted to give Intermediate 23, and the protecting group for one of the carboxyl groups in the resultant Intermediate 23 was deprotected to give Intermediate 24.

Subsequently, Intermediate 20 and Intermediate 24 as prepared in this way were reacted to give Compound 7, and the protecting groups for the carboxyl groups of Compound 7 were deprotected to give Compound 8.

Reaction Scheme 3

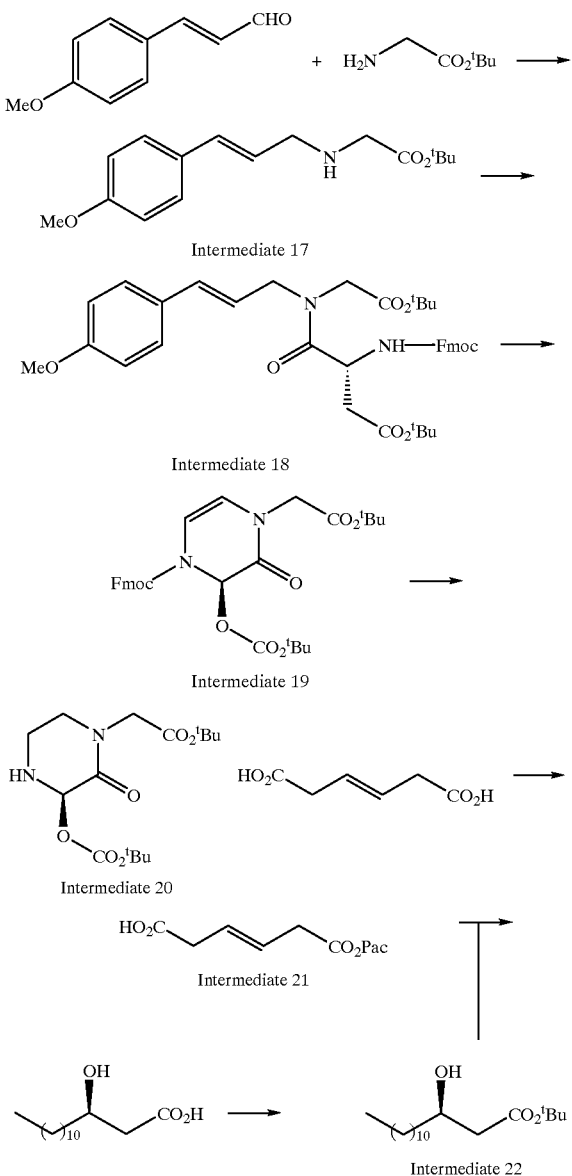

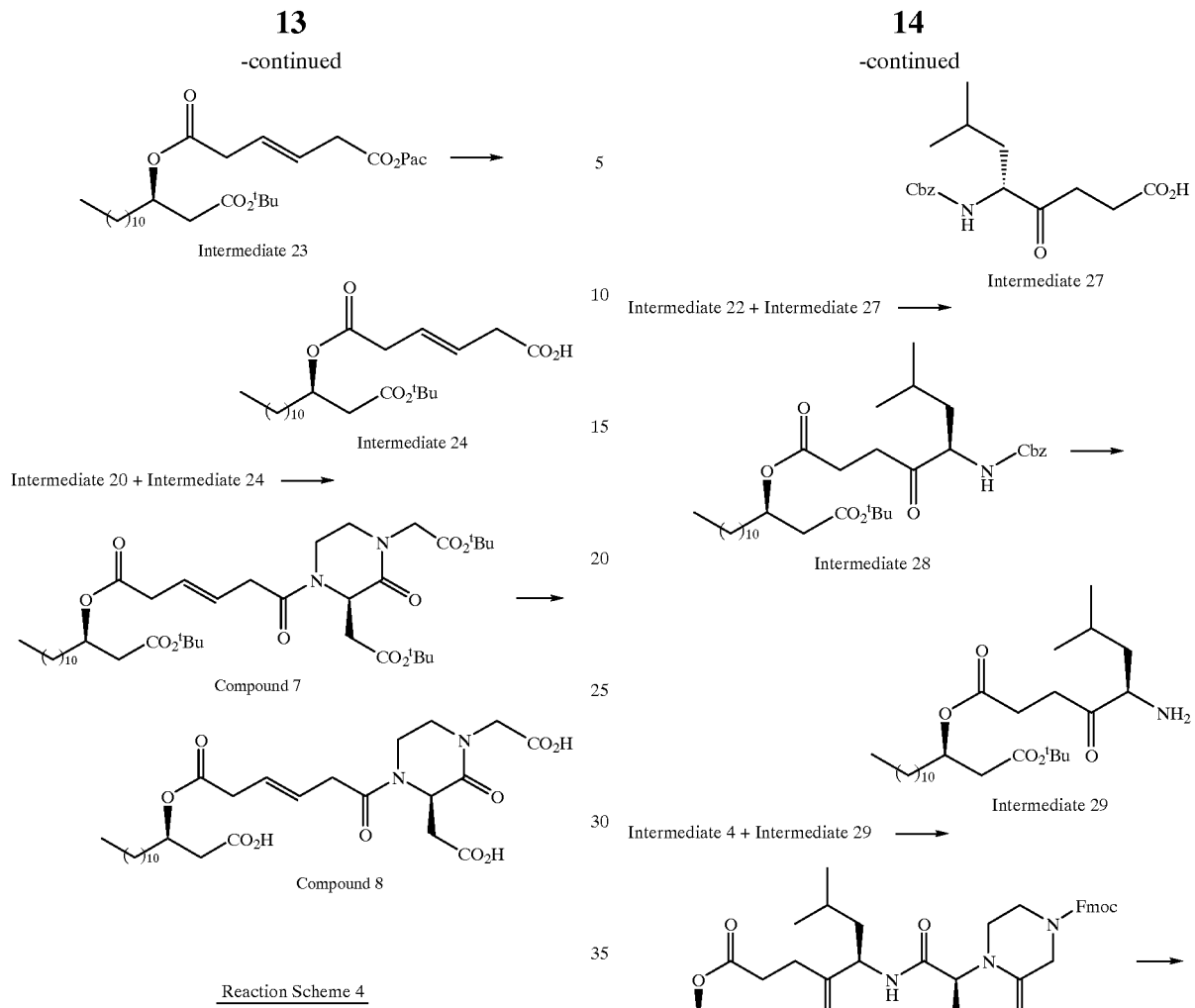

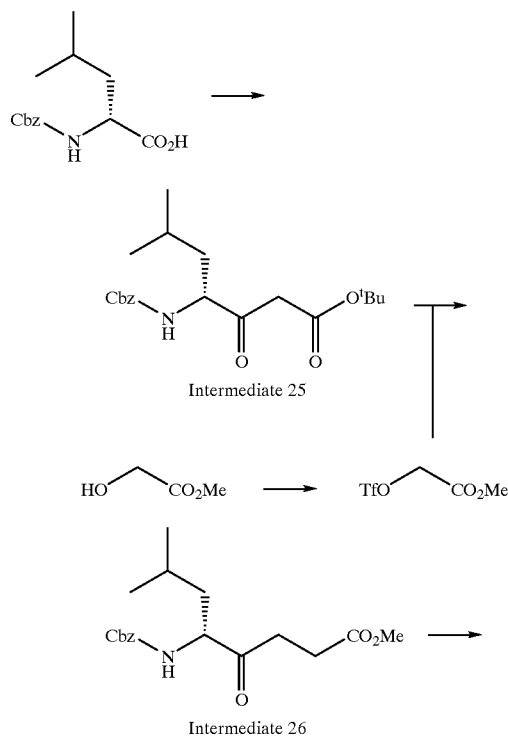

In the reaction procedure according to Reaction Scheme 4, D-leucine having the protected amino group was used as a starting material to prepare Intermediate 25, which was then converted into Intermediate 26. The protecting group for the carboxyl group of Intermediate 26 was removed to give Intermediate 27.

The resultant Intermediate 27 and Intermediate 22 in Reaction Scheme 3 were reacted to give Intermediate 28, and the protecting group for the amino group of the Intermediate 28 was deprotected to give Intermediate 29.

Intermediate 29 and Intermediate 4 in Reaction Scheme 1 were reacted to give Compound 9. The protecting group for the carboxyl group of Compound 9 was deprotected to give Compound 10.

The depsipeptide derivatives containing a piperazinone ring represented by formula (1) prepared according to Reaction Schemes 1–4 or pharmacologically acceptable salts thereof act on a Hep G2 cell which is a cell for the production of apolipoprotein E, thereby potently accelerating the production of apolipoprotein E. Thus they are useful as an accelerator for the production of apolipoprotein E, and also as an agent for the treatment of neurologic injury, an agent for the treatment of dementia and an antihyperlipidemic agent.

The depsipeptide derivatives containing a piperazinone ring or pharmacologically acceptable salts thereof can be formulated into pharmaceutical preparations in various dosage forms. The pharmaceutical preparations include oral preparations, e.g., solid preparations such as tablets, hard capsules, soft capsules, granules and powders, and liquid preparations such as solutions, emulsions and suspensions. The parenteral preparations include injections, suppositories and the like.

The pharmaceutical preparations can be prepared by adding to the depsipeptide derivatives and salts, conventional additives such as excipients, stabilizers, antiseptics, solubilizers, wetting agents, emulsifiers, lubricants, sweetening agents, colorants, flavorings, isotonic agents, buffers, antioxidants and the like.

The additives include starch, sucrose, fructose, lactose, glucose, mannitol, sorbitol, precipitated calcium carbonate, crystalline cellulose, carboxymethylcellulose, dextrin, gelatin, acacia, magnesium stearate, talc, hydroxypropylmethylcellulose and the like.

When the depsipeptide derivatives containing a piperazinone ring or pharmacologically acceptable salts thereof are used as the liquid preparations and injections, they can be dissolved or suspended in any conventional diluent. The diluents include physiological saline, Ringer's solution, aqueous glucose solution, alcohols, fatty acid esters, glycols, glycerol, animal or vegetable fats and oils, paraffins and the like. These preparations can be prepared by a conventional method.

A usual clinical dose is, for oral administration, in the range of 0.5–5000 mg, preferably 5–500 mg per day for adult, and for parenteral administration, in the range of 0.05–5000 mg per day for adult.

EXAMPLE

A process for the preparation of the depsipeptide derivatives is illustrated by the following Examples, a function of accelerating the production of apolipoprotein E by the depsipeptide derivatives is illustrated by the following Test Examples, and illustrative examples of pharmaceutical preparations comprising the depsipeptide Ad derivatives as an active ingredient are given by the following Preparation Examples.

Example 1

The reaction process steps in Example 1 are shown in Reaction Scheme 1. Specific compounds indicated by the numbers of the intermediates and compounds in this example are the same as those shown in Reaction Scheme 1.

i) To a solution of p-methoxycinnamic aldehyde (4.86 g) and L-aspartic acid α-benzyl β-t-butyl ester (8.38 g) in 1,2-dichloroethane (80 ml) was added sodium triacetoxyborohydride (8.48 g) while stirring at room temperature, and the mixture was stirred overnight. The reaction solution was diluted with chloroform, washed with 5% aqueous sodium hydrogencarbonate solution, and dried over anhydrous sodium sulfate. After the solvent was distilled away, the residue was purified by a silica gel column chromatography to afford Intermediate 1 (8.04 g).

$^1$H-NMR (δ ppm, CDCl$_3$) 7.31–7.36 (5H, m), 7.25–7.28 (m, 2H), 6.81–6.85 (2H, m), 6.41 (11, d, J=16 Hz), 6.03–6.10 (1H, m), 5.17 (1H, d, J=12 Hz), 5.15 (1H, d, J=12 Hz), 3.80 (3H, s), 3.68 (1H, t, J=6.3 Hz), 3.43–3.48 (2H, m), 2.59–2.71 (2H, m), 1.41 (9H, s).

ii) To a solution of Intermediate 1 (8.02 g) and Fmoc-glycine (6.74 g) in DMF (30 ml) were added DEPBT (6.81 g) and triethylamine (2.8 ml) while stirring at room temperature, and the mixture was stirred for 5 hours. The solvent was distilled away from the reaction solution, and the residue was purified by a silica gel column chromatography to afford Intermediate 2 (10.3 g).

$^1$H-NMR (δ ppm, CDCl$_3$) 7.76 (2H, d, J=7.8 Hz), 7.61 (2H, d, J=7.3 Hz), 7.38–7.42 (21, m), 7.22–7.33 (7H, m), 7.14 (2H, d, J=8.3 Hz), 6.80 (2H, d, J=8.3 Hz), 6.55 (1H, d, J=16 Hz), 5.92–5.99 (1H, m), 5.73 (1H, br), 5.08–5.15 (2H, m), 4.60–4.63 (1H, m), 4.38 (2H, d, J=7.3 Hz), 4.04–4.24 (5H, m), 3.81 (3H, m), 3.21–3.26 (1H, m), 2.79–2.86 (1H, m), 1.41 (9H, s).

iii) A solution of Intermediate 2 (10.1 g) in a mixed solvent of dichloromethane (100 ml) and methanol (250 ml) was cooled to −70° C., and ozone was introduced until the reaction solution became light blue. Dimethyl sulfide (3.5 ml) was added to the reaction solution, the temperature of which was gradually elevated to room temperature, and the solution was further stirred overnight. The solvent was distilled away from the reaction solution and the residue was purified by a silica gel column chromatography to afford Intermediate 3 (3.57 g).

$^1$H-NMR (δ ppm, CDCl$_3$) 7.88 (2H, d, J=7.8 Hz), 7.64–7.66 (2H, m), 7.39–7.44 (2H, m), 7.30–7.36 (7H, m), 6.16 (1H, br), 5.61 (1H, br), 5.20–5.24 (1H, m), 5.12–5.15 (2H, m), 4.30–4.38 (3H, m), 4.03 (1H, d, J=17 Hz), 3.78 (1H, d, J=17 Hz), 2.88–2.95 (1H, m), 2.61–2.73 (1H, m), 1.36 (9H, s).

iv) To a solution of Intermediate 3 (1.00 g) in methanol (150 ml) was added 10% palladium carbon (0.72 g) and the resultant suspension was stirred under an atmosphere of hydrogen at room temperature for one hour. The catalyst was filtered off and the solvent was distilled away from the filtrate. A solution of sodium carbonate (0.37 g) in water (4 ml) was added to the residue, a solution of N-9-fluorenylmethoxycarbonyl-succinimide (hereinafter referred to as "Fmoc-OSu") (0.58 g) in DMF (8 ml) was added to the resultant suspension under ice-cooling, and the solution was stirred at room temperature for one hour. The reaction solution was diluted with water, and washed with diethyl ether and ethyl acetate. While stirring the aqueous layer on an ice-cooling bath, the layer was adjusted to a pH value of 2 with 6N hydrochloric acid and extracted with chloroform. The organic layer was dried over anhydrous sodium sulfate and the solvent was distilled away. The residue was purified by a silica gel column chromatography to afford Intermediate 4 (0.55 g).

$^1$H-NMR (δ ppm, d6-DMSO) 12.9 (1H, br), 7.87 (2H, d, J=7.3 Hz), 7.61 (2H, d, J=7.8 Hz), 7.39–7.43 (2H, m), 7.31–7.35 (2H, m), 4.98–5.02 (1H, m), 4.39 (2H, d, 6.8 Hz), 4.29 (1H, t, 6.3 Hz), 3.94 (2H, s), 3.23–3.59 (4H, m), 2.85 (1H, dd, J=6.8 Hz, 16 Hz), 2.66 (1H, dd, J=8.3 Hz, 16 Hz), 1.37 (9H, s).

V) To a solution of (R)-3-hydroxymyristic acid (2.50 g) and triethylamine (1.43 ml) in DMF (25 ml) was added phenacyl bromide (2.04 g) at room temperature and the mixture was stirred overnight. After the solvent was distilled away, the residue was diluted with ethyl acetate, washed with water and dried over anhydrous sodium sulfate. After the solvent was distilled away, the residue was purified by a silica gel column chromatography to afford Intermediate 5 (3.53 g).

¹H-NMR (δ ppm, CDCl₃) 7.92 (2H, d, J=6.8 Hz), 7.63 (1H, d, J=7.3 Hz), 7.50 (2H, d, J=7.6 Hz), 5.48 (1H, d, J=17 Hz), 5.37 (1H, d, J=17 Hz), 4.09–4.18 (1H, m), 3.41 (1H, br), 2.70 (1H, dd, J=2.9, 15 Hz), 2.57 (1H, dd, J=9.3, 15 Hz), 1.19–1.67 (20H, m), 0.88 (3H, t, J=6.8 Hz).

vi) To a solution of 5-amino-3-pentenoic acid (1.00 g) in 10% aqueous sodium carbonate solution (20 ml) and dioxane (10 ml) was added a solution of Fmoc-Cl (2.20 g) in dioxane (10 ml) under ice-cooling and the mixture was stirred overnight. The reaction solution was diluted with ethyl acetate and extracted three times with 10% aqueous sodium carbonate solution. The aqueous layer was acidified with 1N hydrochloric acid and then extracted with ethyl acetate. The organic layer was washed successively with water and saturated aqueous sodium chloride solution, and dried over anhydrous sodium sulfate. The solvent was distilled away to afford Intermediate 6 (2.44 g).

¹H-NMR (δ ppm, CDCl₃) 7.75–7.76 (2H, m), 7.57–7.59 (2H, m), 7.37–7.41 (2H, m), 7.28–7.32 (2H, m), 5.50–5.70 (2H, m), 4.88 (1H, m), 4.40–4.43 (2H, m), 4.20–4.30 (1H, m), 3.60–3.82 (2H, m), 3.00–3.12 (2H, m).

vii) To a solution of Intermediate 5 (0.86 g), Intermediate 6 (0.93 g) and DMAP (61 mg) in dichloromethane (30 ml) was added DCC (0.77 g) under ice-cooling and the mixture was stirred under ice-cooling for 2 hours and subsequently at room temperature overnight. After the precipitate was filtered off, the solvent was distilled away. The residue was diluted with ethyl acetate, and washed successively with 10% aqueous citric acid solution, water, 5% aqueous sodium hydrogencarbonate solution and water, and then dried over anhydrous sodium sulfate. After the solvent was distilled away, the residue was purified by a silica gel column chromatography to afford Intermediate 7 (1.54 g).

¹H-NMR (δ ppm, CDCl₃) 7.88 (2H, d, J=6.81 Hz), 7.75 (2H, d, J=7.8 Hz), 7.58 (2H, d, J=7.3 Hz), 7.58.(1H, t, J=7.6 Hz), 7.45 (2H, t, J=7.6 Hz), 7.39 (2H, t, J=7.6 Hz), 7.30 (2H, t, J=7.3 Hz), 5.69–5.80 (1H, m), 5.57–5.68 (1H, m), 5.27–38 (3H, m), 4.99 (11H, br s), 4.36 (2H, d, J=6.8 Hz), 4.19 (1H, t, J=6.6 Hz), 3.81 (2H, br s), 3.05–3.17 (2H, m), 2.77 (1H, dd, J=3.4 Hz), 2.75 (1H, d, J=1.5 Hz), 1.53–1.76 (2H, m), 1.18–1.41 (18H, m), 0.88 (3H, t, J=6.8 Hz).

viii) To a solution of Intermediate 7 (0.33 g) in DMF (5 ml) was added diethylamine (0.5 ml) and the mixture was stirred at room temperature for one hour. After the solvent was distilled away from the reaction solution, the residue was purified by a silica gel column chromatography to afford Intermediate 8 (0.38 g).

¹H-NMR (δ ppm, CDCl₃) 7.89–7.91 (2H, m), 7.59–7.63 (1H, m), 7.47–7.51 (2H, m), 5.70–5.72 (2H, m), 5.28–5.39 (3H, m), 3.30–3.31 (2H, m), 3.09–3.11 (2H, m), 2.71–2.81 (2H, m), 2.17 (2H, br), 1.25–1.30 (20H, m), 0.88 (3H, t, J=6.8 Hz).

ix) To a solution of Intermediate 4 (0.49 g), Intermediate 8 (0.38 g) and HOBt monohydrate (0.17 g) in dichloromethane (15 ml) was added WSCI (0.29 g) under ice-cooling, and the mixture was stirred under ice-cooling for 10 minutes and subsequently at room temperature overnight. The reaction solution was diluted with chloroform, washed with 5% aqueous sodium hydrogencarbonate solution and dried over anhydrous sodium sulfate. After the solvent was distilled away, the residue was purified by a silica gel column chromatography to afford Compound 1 (0.53 g).

1H-NMR (δ ppm, CDCl₃) 7.30–7.90 (13H, m), 6.41 (1H, t, J=5.4 Hz), 5.67–5.72 (1H, m), 5.52–5.59 (1H, m), 5.28–5.42 (4H, m), 2.58–4.45 (17H, m), 1.42 (9H, s), 1.25–1.37 (20H, m), 0.88 (3H, t, J=6.3 Hz).

x) To a solution of Compound 1 (0.49 g) in acetic acid (5 ml) was added zinc powder (1 g) and the mixture was stirred at 50° C. for 2 hours. The insoluble material was filtered off and the solvent was distilled away from the filtrate. The residue was purified by a silica gel column chromatography to afford Compound 2 (0.43 g).

¹H-NMR (δ ppm, CD₃OD) 7.78–7.83 (2H, m), 7.59 (2H, d, J=7.3 Hz), 7.40 (2H, t, J=7.3 Hz), 7.30–7.34 (2H, m), 5.64–35.72 (1H, m), 5.54–5.62 (1H, m), 5.31–5.36 (1H, m), 5.16–5.23 (1H, m), 4.50 (2H, d, J=6.3 Hz), 4.25 (1H, t, J=6.3 Hz), 3.34–4.03 (8H, m), 3.03 (2H, d, J=6.3 Hz), 2.92 (2H, dd, J=6.8 Hz, 16 Hz), 2.55–2.64 (1H, m), 2.53 (2H, d, J=7.3 Hz), 1.42 (9H, S), 1.26–1.38 (20H, m), 0.89 (3H, t, J=6.3 Hz).

xi) To Compound 2 (0.38 g) was added trifluoroacetic acid (hereinafter referred to as "TFA") (1.5 ml) and the mixture was stirred at room temperature for one hour. The reaction solution was diluted with chloroform, washed with water and dried over anhydrous sodium sulfate. After the solvent was distilled away, the residue was purified by a silica gel column chromatography to afford Compound 3 (0.27 g).

¹H-NMR (δ ppm, d6-DMSO) 8.26 (1H, br), 7.86 (2H, d, J=7.8 Hz), 7.61 (2H, d, J=7.8 Hz), 7.41 (2H, t, J=7.3 Hz), 7.33 (2H, t, J=7.3 Hz), 5.54–5.60 (2H, m), 5.25–5.29 (1H, m), 5.08–5.11 (1H, m), 4.25–4.38 (3H, m), 3.88–3.98 (2H, m), 3.33–3.81 (6H, m), 2.90–3.00 (2H, m), 2.73–2.79 (1H, m), 2.32–2.43 (3H, m), 1.21–1.37 (20H, m), 0.84 (3H, t, J=6.8 Hz).

Example 2

The reaction process steps of Example 2 are shown in Reaction Scheme 2. Specific compounds indicated by the numbers of the intermediates and compounds in this example are the same as those shown in Reaction Scheme 2.

i) To a solution of Boc-D-leucine-monohydrate (8.56 g) in THF (80 ml) were added triethylamine (6 ml) and ethyl chloroformate (3.6 ml) under ice-cooling and the mixture was stirred for 45 minutes. After the precipitate was filtered off, the filtrate was added dropwise to a mixed solution of sodium borohydride (3.24 g) in THF (80 ml) and water (20 ml) under ice-cooling over a period of 30 minutes and the mixture was further stirred under ice-cooling for one hour. The reaction solution was concentrated to a volume of about 30 ml under reduced pressure. The residue was diluted with diethyl ether, washed with water and dried over anhydrous magnesium sulfate. After the solvent was distilled away, the residue was purified by a silica gel column chromatography to afford Intermediate 9 (7.14 g).

¹H-NMR (δ ppm, CDCl₃) 4.59 (1H, br), 3.64–3.72 (2H, m), 3.48–3.53 (1H, m), 2.59 (1H, br), 1.63–1.72 (1H, m), 1.45 (9H, s), 1.30–1.33 (2H, m), 0.92–0.94 (6H, m).

ii) To a solution of oxalyl chloride (2.5 ml) in dichloromethane (80 ml) was added dropwise a solution of DMSO (2.99 g) in dichloromethane (8 ml) at −78° C. and the mixture was stirred for 15 minutes. To the reaction solution was added dropwise a solution of Intermediate 9 (3.14 g) in dichloromethane (50 ml) over a period of 10 minutes, and the mixture was stirred at −78° C. for 30 minutes and further at −50° C. for one hour. Diisopropylethylamine (12 ml) was added to the reaction solution, the temperature of which was gradually elevated to room temperature over a period of 30 minutes. Saturated brine was added to the reaction solution, and the organic layer was separated and dried over anhydrous sodium sulfate. The solvent was distilled away to afford Intermediate 10 (7.87 g).

This intermediate was dissolved in 1,2-dichloroethane (200 ml), and D-isoleucine-p-toluenesulfonic acid salt (3.27 g) and sodium triacetoxyborohydride (2.29 g) were added at room temperature and the mixture was stirred for 2 hours.

The reaction solution was washed with aqueous sodium hydrogencarbonate solution and dried over anhydrous sodium sulfate. After the solvent was distilled away, the residue was purified by a silica gel column chromatography to afford Intermediate 11 (3.46 g).

$^1$H-NMR (δ ppm, CDCl$_3$) 7.31–7.39 (5H, m), 5.19 (1H, d, J=12 Hz), 5.12 (1H, d, J=12 Hz), 4.67 (1H, br), 3.69 (1H, br), 3.06 (1H, d, J=5.9 Hz), 2.56–2.61 (1H, m), 2.41–2.44 (1H, m), 1.49–1.70 (4H, m), 1.44 (9H, s), 1.11–1.22 (2H, m), 0.83–0.91 (12H, m).

iii) To a solution of Intermediate 11 (3.46 g) in methanol (200 ml) was added 10% palladium-carbon (0.98 g), and the resultant suspension was stirred under an atmosphere of hydrogen at room temperature for one hour. The catalyst was filtered off and the filtrate was concentrated to a volume of 20 ml under reduced pressure. The precipitated crystals were filtered off and washed with ethanol to afford Intermediate 12 (1.16 g).

Further, the remaining filtrate was concentrated to a volume of 10 ml under reduced pressure and the precipitated crystals were collected by filtration and washed with ethanol to afford Intermediate 12 (0.46 g).

$^1$H-NMR (δ ppm, d6-DMSO) 6.46 (1H, br), 3.59 (1H, br), 2.94 (1H, d, J=5.4 Hz), 2.50–2.59 (2H, m), 1.49–1.64 (3H, m), 1.39 (9H, s), 1.15–1.32 (3H, m), 0.83–0.87 (12H, m).

iv) To a solution of Intermediate 12 (1.59 g) in THF (80 ml) was added a solution of sodium hydrogencarbonate (2.65 g) in water (50 ml), the mixture was stirred under ice-cooling for 10 minutes and then Cbz-Cl (3 ml) was added, and the mixture was further stirred for 3 hours. The reaction solution was concentrated to a volume of about 50 ml under reduced pressure, and chloroform and water were added to the residue. While stirring on an ice bath, the solution was adjusted to a pH value of 4 with 10% aqueous citric acid solution. The organic layer was separated and the aqueous layer was extracted with chloroform. The organic layer was dried over anhydrous magnesium sulfate. After the solvent was distilled away, the residue was purified by a silica gel column chromatography to afford Intermediate 13 (1.96 g).

$^1$H-NMR (δ ppm, CD$_3$OD) 7.29–7.42 (5H, m), 5.17 (1H, d, J=12 Hz), 5.08 (1H, d, J=12 Hz), 3.87–3.98 (2H, m), 3.40–3.45 (1H, m), 3.14–3.19 (1H, m), 2.01 (1H, br), 1.62 (1H, br), 1.42 (9H, s), 0.77–1.28 (16H, m).

v) To a solution of (R)-3-hydroxymyristic acid (3.42 g) in DMF (30 ml) were added triethylamine (2.3 ml) and benzyl bromide (1.8 ml) at room temperature and the mixture was stirred for 2 days. The solvent was distilled away from the reaction solution. The residue was diluted with ethyl acetate, washed with water and dried over anhydrous sodium sulfate. After the solvent was distilled away, the residue was purified by a silica gel column chromatography to afford Intermediate 14 (2.68 g).

$^1$H-NMR (δ ppm, CDCl$_3$) 7.32–7.39 (5H, m), 5.16 (2H, s), 4.01–4.05 (1H, m), 2.83 (1H, d, J=3.9 Hz), 2.56 (1H, dd, J=3.4, 16.6 Hz), 2.46 (1H, dd, J=8.8, 16.6 Hz), 1.41–1.43 (2H, m), 1.25–1.56 (18H, m), 0.88 (3H, t, J=6.8 Hz).

vi) To a solution of Intermediate 13 (1.46 g), Intermediate 14 (1.34 g) and DMAP (40 mg) in dichloromethane (10 ml) was added DCC (0.97 g) under ice-cooling, and the mixture was stirred under ice-cooling for 30 minutes and subsequently at room temperature overnight. The precipitate was filtered off, and the filtrate was washed successively with 10% aqueous citric acid solution and water, and dried over anhydrous sodium sulfate. After the solvent was distilled away, the residue was purified by a silica gel column chromatography to afford Intermediate 15 (1.09 g).

$^1$H-NMR (δ ppm, d6-DMSO) 7.27–7.37 (10H, m), 6.44 (1H, br), 4.98–5.13 (5H, m), 4.06 (1H, br), 3.74 (1H, br), 3.25–3.31 (1H, m), 3.01–3.06 (1H, m), 2.59–2.64 (2H, m), 2.00 (1H, br), 1.00–1.82 (32H, m), 0.82–0.87 (15H, m).

vii) Intermediate 15 (1.29 g) was dissolved in TFA (5 ml) and the mixture was stirred at room temperature for 90 minutes. After the solvent was distilled away from the reaction solution, chloroform and water were added to the residue, and the aqueous layer was adjusted to a pH value of 8 with 5% aqueous sodium hydrogencarbonate solution. The organic layer was separated and the aqueous layer was extracted with chloroform. The organic layer was dried over anhydrous sodium sulfate, and the solvent was distilled away to afford Intermediate 16 (1.08 g). 0.54 g of Intermediate 16 was dissolved in dichloromethane (5 ml), and HOAt (0.12 g), diisopropylethylamine (0.22 ml), HATU (0.37 g) and a solution of Intermediate 4 (0.41 g) in dichloromethane (5 ml) were added successively under ice-cooling. The temperature of the mixture was gradually elevated to room temperature and the mixture was further stirred overnight. The reaction solution was diluted with chloroform, washed with 10% aqueous citric acid solution and dried over anhydrous sodium sulfate. After the solvent was distilled away, the residue was purified by a silica gel column chromatography to afford Compound 4 (0.79 g).

$^1$H-NMR (δ ppm, d6-DMSO) 7.86 (2H, d, J=7.8 Hz), 7.71 (1H, br), 7.60 (2H, d, J=5.3 Hz), 7.31–7.42 (14H, m), 4.94–5.23 (6H, m), 4.25–4.37 (3H, m), 3.92–3.99 (3H, m), 3.08–3.55 (7H, m), 2.41–2.80 (4H, m), 2.02 (1H, br), 0.97–1.51 (34H, m), 0.75–0.86 (15H, m).

viii) To a solution of Compound 4 (0.64 g) in methanol (40 ml) was added 10% palladium-carbon (138 mg), and the resultant suspension was stirred under an atmosphere of hydrogen at room temperature for 5 hours. The catalyst was filtered off and the solvent was distilled away from the filtrate. The residue was dissolved in methanol (40 ml), 10% palladium-carbon (110 mg) was added, and the resultant suspension was stirred under an atmosphere of hydrogen at room temperature for 40 minutes. The catalyst was filtered off and the solvent was distilled away from the filtrate. The residue was purified by a silica gel column chromatography to afford Compound 5 (0.35 g).

$^1$H-NMR (δ ppm, d6-DMSO) 7.87 (2H, d, J=7.3 Hz), 7.61 (2H, d, J=7.8 Hz), 7.31–7.46 (5H, m), 5.09–5.22 (2H, m), 4.26–4.38 (3H, m), 3.90–4.01 (3H, m), 3.18–3.63 (5H, m), 2.76–2.93 (2H, m), 2.28–2.56 (4H, m), 1.02–1.54 (35H, m), 0.79–0.86 (15H, m).

ix) Compound 5 (0.34 g) was dissolved in TFA (3 ml) and the mixture was stirred at room temperature for 90 minutes. After the solvent was distilled away from the reaction solution, diethyl ether (2 ml) was added to the residue to form a homogeneous solution. This solution was added dropwise to ice-cooled hexane (15 ml) and the precipitate was separated out. The supernatant solution was removed and the remaining precipitate was dried under reduced pressure to afford a trifluoroacetate salt of Compound 6 (0.34 g).

1H-NMR (δ ppm, d6-DMSO) 12.3 (1H, br), 8.70 (1H, br), 7.87 (2H, d, J=7.3 Hz), 7.62 (2H, d, J=7.3 Hz), 7.39–7.43 (2H, m), 7.31–7.35 (2H, m), 5.23–5.27 (1H, m), 4.55–4.59 (1H, m), 3.50–4.39 (11H, m), 2.85–3.02 (2H, m), 2.49–2.62 (4H, m), 1.98–2.02 (1H, m), 1.20–1.61 (34H, m), 0.80–0.96 (15H, m).

Example 3

The reaction process steps of Example 3 are shown in Reaction Scheme 3. Specific compounds indicated by the numbers of the intermediates and compounds in this example are the same as those shown in Reaction Scheme 3.

i) To a solution of p-methoxycinnamic aldehyde (7.00 g) and L-glycine tert-butyl ester (7.25 g) in 1,2-dichloroethane (400 ml) was added sodium triacetoxyborohydride (12.7 g) at room temperature while stirring, and the mixture was stirred for one hour. The reaction solution was washed with 5% aqueous sodium hydrogencarbonate solution and dried over anhydrous sodium sulfate. After the solvent was distilled away, the residue was purified by a silica gel column chromatography to afford Intermediate 17 (3.56 g).

$^1$H-NMR (δ ppm, CDCl$_3$) 7.28–7.32 (1H, m), 6.83–6.86 (1H, m), 6.47 (1H, d, J=16 Hz), 6.11 (1H, td, J=6.3 Hz, 16 Hz), 3.80 (3H, s), 3.39 (2H, dd, J=1.5 Hz, 6.3 Hz), 3.33 (2H, m), 1.46 (91, m).

ii) To a solution of Intermediate 17 (6.02 g) and Fmoc-D-aspartic acid β-tert-butyl ester (9.99 g) in DMF (30 ml) were added DEPBT (7.40 g) and triethylamine (3.2 ml) at room temperature while stirring, and the mixture was stirred overnight. After the solvent was distilled away from the reaction solution, the residue was purified by a silica gel column chromatography to afford Intermediate 18 (14.2 g).

$^1$H-NMR (δ ppm, CDCl$_3$) 7.75 (2H, d, J=7.8 Hz), 7.54–7.60 (2H, m), 7.37–7.41 (2H, m), 7.26–7.32 (4H, m), 6.77–6.83 (2H, m), 6.42–6.52 (1H, m), 5.90–6.07 (1H, m), 5.70–5.74 (1H, m), 4.83–5.14 (1H, m), 3.92–4.40 (7H, m), 3.76 (3H, m), 2.74–2.81 (1H, m), 2.56–2.65 (1H, m), 1.43 (9H, s).

iii) A solution of Intermediate 18 (14.0 g) in a mixed solvent of dichloromethane (100 ml) and methanol (250 ml) was cooled to −70° C., and ozone was introduced until the reaction solution became light blue. Dimethyl sulfide (5 ml) was added to the reaction solution, the temperature of which was gradually elevated to room temperature, and the solution was further stirred overnight. The solvent was distilled away from the reaction solution and the residue was purified by a silica gel column chromatography to afford Intermediate 19 (11.3 g).

$^1$H-NMR (δ ppm, d6-DMSO) 7.81–7.87 (2H, m), 7.67 (2H, d, J=7.3 Hz), 7.39–7.42 (2H, m), 7.30–7.35 (2H, m), 4.89 (1H, br), 4.79 (1H, br), 4.53–4.61 (2H, m), 4.28–4.32 (2H, m), 3.58 (1H, d, J=13 Hz), 3.49 (1H, d, J=13 Hz), 2.43–2.61 (2H, m), 1.42 (9H, s), 1.36 (9H, s).

iv) To a solution of Intermediate 19 (2.85 g) in methanol (200 ml) was added 10% palladium-carbon (2.66 g), and the resultant suspension was stirred under an atmosphere of hydrogen at room temperature for 7 hours. The catalyst was filtered off and the solvent was distilled away from the filtrate. The residue was purified by a silica gel column chromatography to afford Intermediate 20 (0.70 g).

$^1$H-NMR (δ ppm, CDCl$_3$) 4.14 (1H, d, J=17 Hz), 3.83 (1H, d, J=17 Hz), 3.76 (1H, dd, J=2.9 Hz, 9.3 Hz), 3.52–3.58 (1H, m), 3.08–3.27 (3H, m), 2.98 (1H, dd, J=2.9 Hz, 17 Hz), 2.64 (1H, dd, J=9.3 Hz, 17 Hz), 1.47 (9H, s), 1.45 (9H, s).

v) To a solution of trans-2-butene-1,4-dicarboxylic acid (3.00 g) and triethylamine (3.2 ml) in DMF (50 ml) was added a solution of phenacyl bromide (4.14 g) in DMF (20 ml) at room temperature and the mixture was stirred overnight. The insoluble material was filtered off and the solvent was distilled away from the filtrate. The residue was purified by a silica gel column chromatography to afford Intermediate 21 (3.02 g).

$^1$H-NMR (δ ppm, CDCl$_3$) 7.90–7.92 (2H, m), 7.59–7.63 (1H, m), 7.47–7.51 (2H, m), 5.72–5.83 (2H, m), 5.36 (2H, s), 3.29–3.31 (2H, m), 3.15–3.17 (2H, m).

vi) (R)-3-hydroxymyristic acid (1.67 g) was suspended in tert-butyl acetate (40 ml), boron trifluoride-diethyl ether complex (3.5 ml) was added while stirring under ice-cooling, and the mixture was stirred for 4.5 hours. Water was added to the reaction solution, and the organic layer was separated and dried over anhydrous sodium sulfate. After the solvent was distilled away, the residue was purified by a silica gel column chromatography to afford Intermediate 22 (1.35 g).

1H-NMR (δ ppm, CDCl$_3$) 3.93–3.98 (1H, m), 3.07 (1H, d, J=3.9 Hz), 2.43 (1H, dd, J=2.9 Hz, 17 Hz), 2.31 (1H, dd, J=9.2 Hz, 17 Hz), 1.19–1.52 (29H, m), 0.88 (3H, t, J=6.8 Hz).

vii) To a solution of Intermediate 21 (0.31 g), Intermediate 22 (0.30 g) and DMAP (25 mg) in dichloromethane (3 ml) was added DCC (0.31 g) under ice-cooling, and the mixture was stirred under ice-cooling for 5 minutes and subsequently at room temperature for 30 minutes. After the precipitate was filtered off, the solvent was distilled away. The residue was purified by a silica gel column chromatography to afford Intermediate 23 (0.46 g).

$^1$H-NMR (B ppm, CDCl$_3$) 7.90–7.92 (2H, m), 7.59–7.64 (1H, m), 7.47–7.51 (2H, m), 5.74–5.76 (2H, m), 5.35 (2H, S), 5.17–5.25 (1H, m), 3.27–3.29 (2H, m), 3.08–3.09 (2H, m), 2.42–2.53 (2H, m), 1.43 (9H, s), 1.24–1.39 (20H, m), 0.87 (3H, t, J=6.8 Hz).

viii) To a solution of Intermediate 23 (0.51 g) in acetic acid (10 ml) was added zinc powder (1.77 g), and the mixture was stirred at 50° C. for 3.5 hours. The insoluble material was filtered off and the filtrate was concentrated. The residue was purified by a silica gel column chromatography to afford Intermediate 24 (0.39 g).

$^1$H-NMR (δ ppm, CDCl$_3$) 5.63–5.76 (2H, m), 5.18–5.35 (1H, m), 3.13 (2H, d, J=5.4 Hz), 3.07 (2H, d, J=5.4 Hz), 2.42–2.53 (2H, m), 1.43 (9H, s), 1.24–1.36 (20H, m), 0.88 (3H, t, J=6.8 Hz).

ix) Intermediate 24 (0.39 g) was dissolved in dichloromethane (5 ml), and HOAt (0.14 g), diisopropylethylamine (0.32 ml), HATU (0.42 g) and a solution of Intermediate 20 (0.40 g) in dichloromethane (6 ml) were successively added under ice-cooling. The temperature of the solution was gradually elevated to room temperature and the mixture was stirred for 6.5 hours. The reaction solution was diluted with chloroform, washed with 10% aqueous citric acid solution and dried over anhydrous sodium sulfate. After the solvent was distilled away, the residue was purified by a silica gel column chromatography to afford Compound 7 (0.61 g).

$^1$H-NMR (δ ppm, CDCl$_3$) 5.67–5.70 (2H, m), 5.17–5.20 (1H, m), 4.82–4.86 (1H, m), 3.82–4.21 (3H, m), 3.52–3.68 (1H, m), 2.74–3.32 (8H, m), 2.41–2.52 (2H, m), 1.46 (9H, s), 1.44 (9H, s), 1.42 (9H, s), 1.24–1.27 (20H, m), 0.87 (3H, t, J=6.8 Hz).

x) To Compound 7 (0.57 g) was added TFA (4 ml), and the mixture was stirred at room temperature for 90 minutes. After the solvent was distilled away from the reaction solution, diethyl ether (2 ml) was added to the residue to form a homogeneous solution. This solution was added dropwise to ice-cooled hexane (15 ml) and the precipitate was separated out. The supernatant solution was removed and the remaining precipitate was dried under reduced pressure to afford Compound 8 (0.32 g).

$^1$H-NMR (δ ppm, d6-DMSO) 12.3 (3H, br), 5.57–5.67 (2H, m), 5.04–5.11 (1H, m), 4.90–4.93 (1H, m), 3.87–4.21 (3H, m), 2.66–3.66 (9H, m), 2.42–2.53 (2H, m), 1.23–1.30 (20H, m), 0.86 (3H, t, J=6.8 Hz).

Example 4

The reaction process steps of Example 4 are shown in Reaction Scheme 4. Specific compounds indicated by the A numbers of the intermediates and compounds in this example are the same as those shown in Reaction Scheme 4.

i) To a solution of Z-D-leucine (5.30 g) in THF (80 ml) was added 1,1'-carbonyldiimidazole (3.41 g) at room temperature, and the mixture was stirred for 2 hours.

To a solution of diisopropylamine (8.83 ml) in THF (20 ml) was added an n-hexane solution (38.7 ml) of n-BuLi (1.63 M) at −20° C., and the mixture was stirred for 20 minutes. To this solution was added t-butyl acetate (8.49 ml) at −78° C., and the mixture was stirred for 30 minutes. To this mixture was added at −78° C. an imidazole solution as prepared previously. After stirring the mixture at this temperature for one hour, 1N hydrochloric acid solution was added and the mixture was extracted twice with ethyl acetate. The organic layer was washed with water and saturated brine, and dried over anhydrous magnesium sulfate. After the solvent was distilled away, the residue was purified by a silica gel column chromatography to afford Intermediate 25 (5.09 g).

$^1$H-NMR (δ ppm, CDCl$_3$) 7.27–7.40 (5H, m), 5.21 (1H, d, J=8.8 Hz), 5.11 (2H, s), 4.47 (1H, dt, J=3.7, 9.3 Hz), 3.50 (1H, d, J=15 Hz), 3.42 (1H, d, J=16 Hz), 1.46 (9H, s), 1.35–1.80 (3H, m), 0.97 (3H, d, J=5.9 Hz), 0.94 (3H, d, J=6.3 Hz).

ii) To a suspension of NaH (60%, 0.39 g) in THF (50 ml) was added dropwise a solution of Intermediate 25 (3.30 g) in THF (130 ml) under ice-cooling. After stirring the mixture for 10 minutes, a solution of methyl bromoacetate (1.7 ml) in THF (5 ml) was added. After the reaction solution was stirred at room temperature overnight, 1N hydrochloric acid solution was added, and the solution was extracted with ethyl acetate. The resultant organic layer was washed with saturated brine and dried over anhydrous magnesium sulfate. After the solvent was distilled away, the residue was dissolved in dichloromethane (50 ml). TFA (16 ml) was added and the solution was stirred at room temperature for 2 days. After the solvent was distilled away, chloroform and saturated aqueous sodium hydrogencarbonate solution were added. The resultant organic layer was washed with saturated aqueous sodium hydrogencarbonate solution and saturated brine, and dried over anhydrous magnesium sulfate. After the solvent was distilled away, the residue was purified by a silica gel column chromatography to afford Intermediate 26 (2.59 g).

$^1$H-NMR (δ ppm, CDCl$_3$) 7.28–7.41 (5H, m), 5.21 (1H, d, J=7.8 Hz), 5.10 (2H, s), 4.42 (1H, dt, J=4.4, 9.3 Hz), 3.67 (3H, s), 2.85–2.96 (1H, m), 2.72–2.83 (1H, m), 2.51–2.71 (2H, m), 1.55–1.81 (2H, m), 1.31–1.45 (1H, m), 0.98 (3H, d, J=6.3 Hz), 0.94 (3H, d, J=6.3 Hz).

iii) To a solution of Intermediate 27 (2.50 g) in a mixed solvent of THF (45 ml) and water (45 ml) was added lithium hydroxide monohydrate (0.63 g), and the mixture was stirred at room temperature for 30 minutes. Diethyl ether and saturated aqueous sodium hydrogencarbonate solution were added, and the resultant aqueous layer was adjusted to a pH value of 3 with 6N hydrochloric acid solution and extracted with ethyl acetate. The organic layer was dried over anhydrous magnesium sulfate, and the solvent was distilled away. The residue was purified by a silica gel column chromatography to afford Intermediate 27 (2.40 g).

$^1$H-NMR (δ ppm, CDCl$_3$) 7.28–7.40 (5H, m), 5.24 (1H, d, J=8.3 Hz), 5.10 (2H, s), 4.42 (1H, dt, J=3.9, 8.8 Hz), 2.52–2.94 (4H, m), 1.58–1.78 (2H, m), 1.34–1.42 (1H, m), 0.97 (3H, d, J=6.3 Hz), 0.93 (3H, d, J=6.3 Hz).

iv) To a solution of Intermediate 22 (0.80 g), Intermediate 27 (0.94 g) and DMAP (22 mg) in dichloromethane (20 ml) was added DCC (0.82 g) under ice-cooling. The reaction solution was stirred under ice-cooling for 2 hours and at room temperature overnight. After filtration and concentration, ethyl acetate and 10% aqueous citric acid solution were added. The resultant organic layer was washed with water, 5% aqueous sodium hydrogencarbonate solution and water, and then dried over anhydrous sodium sulfate. After the solvent was distilled away, the residue was purified by a silica gel column chromatography to afford Intermediate 28 (1.31 g).

$^1$H-NMR (δ ppm, CDCl$_3$) 7.28–7.41 (5H, m), 5.14–5.29 (2H, m), 5.10 (2H, s), 4.36–4.46 (1H, m), 2.38–2.95 (6H, m), 1.50–1.80 (3H, m), 1.43 (9H, s), 1.17–1.45 (20H, m), 0.98 (3H, d, J=5.9 Hz), 0.94 (3H, d, J=6.3 Hz), 0.88 (3H, t, J=6.8 Hz).

v) To a solution of Intermediate 28 (1.20 g) in methanol (30 ml) was added 5% palladium-carbon (0.25 g), and the resultant suspension was stirred under an atmosphere of hydrogen at room temperature for one hour. The catalyst was filtered off, and the solvent was distilled away from the filtrate to afford Intermediate 29 (0.86 g).

vi) To a solution of the resultant Intermediate 29 (0.43 g), Intermediate 4 (0.41 g) and HOBt monohydrate (0.12 g) in dichloromethane (10 ml) was added WSCI (0.15 g) under ice-cooling, and the mixture was stirred under ice-cooling for 2 hours and subsequently at room temperature overnight. Ethyl acetate and 10% aqueous citric acid solution were added. The resultant organic layer was washed with water, 5% aqueous sodium hydrogencarbonate solution and water, and then dried over anhydrous sodium sulfate. After the solvent was distilled away, the residue was purified by a silica gel column chromatography to afford Compound 9 (80 mg).

$^1$H-NMR (δ ppm, CDCl$_3$) 7.77 (2H, d, J=7.8 Hz), 7.56 (2H, d, J=7.3 Hz), 7.41 (2H, t, J=7.3 Hz), 7.32 (2H, t, J=7.6 Hz), 6.57 (1H, d, J=6.8 Hz), 5.49–5.57 (1H, m), 5.16 (1H, quint., J=6.1 Hz), 4.33–4.58 (3H, m), 4.24 (1H, t, J=6.6 Hz), 3.96–4.16 (2H, m), 3.33–3.50 (2H, m), 3.10–3.29 (2H, m), 2.78–2.98 (2H, m), 2.37–2.73 (6H, m), 1.49–1.79 (3H, m), 1.42 (9H, s), 1.41 (9H, s), 1.16–1.33 (20H, m), 0.95 (6H, d, J=6.8 Hz), 0.87 (3H, t, J=6.8 Hz).

vii) TFA (1 ml) was added to Compound 9 (80 mg) and the mixture was stirred at room temperature for one hour. The solvent was distilled away from the filtrate to afford Compound 10 (71 mg).

$^1$H-NMR (δ ppm, d6-DMSO) 8.22 (1H, d, J=7.8 Hz), 7.88 (2H, d, J=7.3 Hz), 7.62(2H, d, J=7.3 Hz), 7.41 (2H, t, J=7.3 Hz), 7.33 (2H, t, J=7.3 Hz), 5.21 (1H, t, J=6.8 Hz), 5.03 (1H, quint., J=6.2 Hz), 4.37 (2H, d, J=6.3 Hz), 4.22–4.31 (2H, m), 3.94 (2H, s), 3.57–3.67 (1H, m), 3.42–3.55 (1H, m), 3.30 (2H, t, J=4.9 Hz), 2.86 (1H, dd, J=7.8, 16 Hz), 2.64–2.72 (2H, m), 2.36–2.54 (7H, m), 1.41–1.66 (3H, m), 1.11–1.30 (20H, m), 0.88 (3H, d, J=6.3 Hz), 0.79–0.86 (6H, m).

Test Example

The effect of the depsipeptide derivatives containing a piperazinone ring on the abilities of producing apolipoprotein E and apolipoprotein B in Hep G2 cells is illustrated below, together with the test method.

First, Hep G2 cells of 1×10$^5$ cells/ml were suspended in Dulbecco's modified Eagle medium (manufactured by Nissui Seiyaku Co., Ltd.; hereinafter referred to as "D-MEM medium") containing 10% fetal bovine serum and 1 ml each of the suspension was poured into a 24-well tissue culture plate. The cells were cultivated at 37° C. under an atmosphere of a mixed gas composed of 5% carbon dioxide and 95% air. After 3 days, the medium was removed by means of a 39 pipette, and 1 ml of a fresh D-MEM medium was added. Further, 10 μl of a methanol solution each of Compound 3, TFA salt of Compound 6, Compound 8 and Compound 10 which were the depsipeptide derivatives containing a piperazinone ring of the invention was added at the concentration of each compound as shown in Table 1. After 18 hours, the medium (D-MEM medium) was again replaced, 10 μl of the methanol solution each of the depsipeptide derivatives containing a piperazinone ring was added, and cultivation was further conducted at 37° C. for 8 hours. The supernatant was used as a sample solution. The apolipoprotein E produced in the cultured broth was assayed by means of an enzyme immunoassay method.

The compositions of the buffers used in the enzyme immunoassay method are summarized below. PBS stands for a phosphate buffered saline, PBS-T stands for a phosphate buffered saline containing Tween 20, and a blocking solution is a phosphate buffered saline containing an immunosuppressive agent "Block Ace" attributable to lactoprotein which is manufactured by Dainippon Pharmaceutical Co., Ltd.

| PBS (pH 7.2) | |
| --- | --- |
| $KH_2PO_4$ | 0.2 g |
| $Na_2HPO_4.12H_2O$ | 2.9 g |
| NaCl | 8.0 g |
| KCl | 0.2 g |
| Distilled water | q.s. |
| Total | 1000 ml |

| PBS-T (pH 7.2) | |
| --- | --- |
| $KH_2PO_4$ | 0.2 g |
| $Na_2HPO_4.12H_2O$ | 2.9 g |
| NaCl | 8.0 g |
| KCl | 0.2 g |
| Tween 20 | 0.5 g |
| Distilled water | q.s. |
| Total | 1000 ml |

| Blocking solution (pH 7.2) | |
| --- | --- |
| Block Ace | 250 ml |
| $KH_2PO_4$ | 0.2 g |
| $Na_2HPO_4.12H_2O$ | 2.9 g |
| NaCl | 8.0 g |
| KCl | 0.2 g |
| Distilled water | q.s. |
| Total | 1000 ml |

1) Determination of Apolipoprotein E

The mouse antihuman apolipoprotein E monoclonal antibody (manufactured by BYOSIS, S. A., France) was dissolved in a 0.05M aqueous sodium hydrogencarbonate solution (pH 9.5) at a concentration of 5 μg/ml. 50 μl each of the solution was poured into Nunc immunoplates, which were then allowed to stand at 4° C. for 16 hours. They were washed three times with 300 μl of PBS, 300 μl of the blocking solution was added, and the mixture was allowed to stand at 37° C. for 2 hours and then at 4° C. for 16 hours.

It was again washed three times with 300 μl of IPBS, 50 μl of the above sample solution (the medium for Hep G2 cells) was added, and the mixture was allowed to stand at room temperature for 2 hours. After washing the mixture three times with 300 μl of PBS-T, 50 μl of a 3000-fold diluted solution (10% aqueous Block Ace solution) of goat anti-apolipoprotein E polyclonal antibody (manufactured by Chemicon Co., Ltd., U.S.A.) was added and the mixture was allowed to stand at room temperature for 2 hours. The mixture was washed three times with 300 μl of PBS-T, a 5000-fold diluted solution (10% aqueous Block Ace solution) of a peroxidase-labeled anti-goat IgG polyclonal antibody (manufactured by Bindingsite Co., Ltd., U.K.) was added and the mixture was allowed to stand at room temperature for 2 hours. After washing the mixture five times with 300 μl of PBS-T, 100 μl of a coloring solution (Composition: 1 ml of 0.1M potassium citrate (pH 4.5), 0.4 μl of 30% aqueous hydrogen peroxide, 1 mg of o-phenylenediamine) was added and the mixture was allowed to stand for 2 minutes. The reaction was quenched by the addition of 100 μl of 2N sulfuric acid and absorbance was measured at 490 nm using absorbance at 650 nm as a control. An amount of apolipoprotein E in the depsipeptide derivative containing a piperazinone ring of the invention was determined upon the calibration curve drawn up when a commercially available apolipoprotein E (Chemicon Co., Ltd., U.S.A.) was used as a standard.

In the Test Example, the same procedure as described above was carried out except that methanol was added alone instead of the methanol solution of the depsipeptide derivative containing a piperazinone ring of the invention and an apolipoprotein E amount was measured as a control. A relative apolipoprotein E amount by the depsipeptide derivative containing a piperazinone ring of the invention was expressed as a relative value (%) in terms of the control defined as 100.

As shown in Table 1, it was proved that the depsipeptide derivatives containing a piperazinone ring of the invention could strongly accelerate the ability of producing apolipoprotein E at a concentration of 1 or 5 μM.

TABLE 1

| Depsipeptide derivatives having a piperazinone ring | Conc. (μM) | Relative amount of apolipoprotein E (%) |
| --- | --- | --- |
| Compound 3 | 1 | 222 |
| Compound 3 | 5 | 373 |
| TFA salt of Compound 6 | 1 | 280 |
| TFA salt of Compound 6 | 5 | 458 |
| Compound 8 | 1 | 156 |
| Compound 10 | 1 | 228 |
| Compound 10 | 5 | 458 |
| Control | 0 | 100 |

Preparation Example

| Preparation Example 1: Tablets (per tablet) | |
| --- | --- |
| Compound 10 | 20 mg |
| Magnesium silicate | 20 mg |
| Lactose | 98.5 mg |
| Hydroxypropylcellulose | 7.5 mg |
| Magnesium stearate | 1 mg |
| Hydrogenated vegetable oil | 3 mg |
| Total | 150 mg |

Compound 10, magnesium silicate and lactose were admixed, and the mixture was kneaded with an alcoholic solution of hydroxypropylcellulose and then granulated to appropriate particle size, dried and sized. Then, magnesium stearate and hydrogenated vegetable oil were added and

| Preparation Example 2: Granules | |
|---|---|
| Compound 10 | 10 mg |
| Magnesium oxide | 40 mg |
| Dibasic calcium phosphate | 38 mg |
| Lactose | 10 mg |
| Hydroxypropylcellulose | 20 mg |

All materials of the above formulation except for hydroxypropylcellulose were uniformly admixed, and the mixture was kneaded with an alcohol solution of hydroxypropylcellulose and then granulated by means of an extrusion granulation machine and dried to from granules. The granules were sized so as to pass through a 12-mesh sieve and remain on a 48-mesh sieve, whereby granules were prepared.

| Preparation Example 3: Syrups | |
|---|---|
| TFA salt of Compound 6 | 1.000 g |
| Sucrose | 30.000 g |
| D-Sorbitol 70 w/v % | 25.000 g |
| Ethyl paraoxybenzoate | 0.030 g |
| Propyl paraoxybenzoate | 0.015 g |
| Flavoring agent | 0.200 g |
| Glycerol | 0.150 g |
| 96% Ethanol | 0.500 g |
| Purified water | q.s. |
| Total | 100 ml |

Sucrose, D-sorbitol, ethyl paraoxybenzoate, propyl paraoxybenzoate and TFA salt of Compound 6 were dissolved in 60 g of purified water (warm water). After cooling, a solution of flavoring agent in glycerol and ethanol was added and then purified water was added to the mixture to make up a volume to 100 ml.

| Preparation Example 4: Injections | |
|---|---|
| TFA salt of Compound 6 | 10.0 mg |
| Sodium chloride | 81.0 mg |
| Sodium hydrogencarbonate | 8.40 mg |
| Distilled water for injection | q.s. |
| Total | 10.0 ml |

Sodium hydrogencarbonate, sodium chloride and TFA salt of Compound 6 were dissolved in distilled water to make up a total amount to 10.0 ml.

| Preparation Example 5: Suppositions | |
|---|---|
| Compound 10 | 2 g |
| Macrogol 4000 | 20 g |
| Glycerol | 78 g |
| Total | 100 g |

Compound 10 was dissolved in gylcerol, and then Macrogol 4000 was added and dissolved by warming. Then, the mixture was injected into a suppository die and solidified by cooling to prepare suppositories, each weighing 1.5 g.

What is claimed is:

1. A depsipeptide derivative containing a piperazinone ring represented by formula (1)

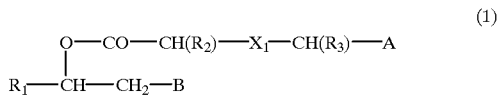

wherein
$X_1$ represents $N(R_4)$—CO, $N(R_5)$—$CH_2$, $CH_2$—CO, $CH_2$—$CH_2$, CH=CH, $CH_2$—CH(OH) or CH(OH)—CH(OH), $R_1$ represents a $C_5$–$C_{20}$ alkyl group or a $C_5$–$C_{15}$ alkoxy $C_1$–$C_4$ alkyl group, $R_2$–$R_5$ represent a hydrogen atom or a $C_1$–$C_6$ alkyl group, A represents a group of formula (2), (3) or (4)

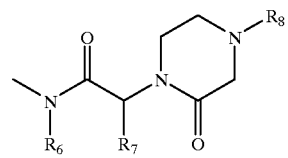

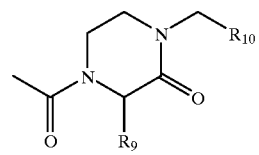

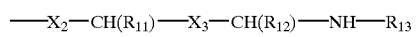

wherein $X_2$ and $X_3$ each independently represent $N(R_{14})$—CO, $N(R_{15})$—$CH_2$, $CH_2$—CO, $CH_2$—$CH_2$, CH=CH, $CH_2$—CH(OH) or CH(OH)—CH(OH), $R_6$, $R_{12}$, $R_{14}$ and $R_{15}$ represent a hydrogen atom or a $C_1$–$C_6$ alkyl group, $R_7$, $R_9$ and $R_{11}$ represent $(CH_2)_{m1}$—COOH wherein $m_1$ represents an integer of 1–3 or $(CH_2)_{n1}$—$CONH_2$ wherein $n_1$ represents 2 or 3, $R_8$ and $R_{13}$ represent a hydrogen atom or an amine-protecting group, and $R_{10}$ represents a hydrogen atom, a $C_1$–$C_6$ alkyl group, a carboxyl group or a $C_1$–$C_6$ alkoxycarbonyl group, and B represents a carboxyl group, a $C_1$–$C_6$ alkoxycarbonyl group or a group of formula (5)

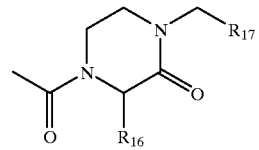

wherein $R_{16}$ represents $(CH_2)_{m2}$—COOH wherein $m_2$ represents an integer of 1–3 or $(CH_2)_{n2}$—$CONH_2$ wherein $n_2$ represents 2 or 3, and $R_{17}$ represents a hydrogen atom, a $C_1$–$C_6$ alkyl group, a carboxyl group or a $C_1$–$C_6$ alkoxycarbonyl group, provided that the carboxyl group in the above-mentioned A and B may be protected by an protecting group, and that when A is a group represented by formula (4), B is a group represented by formula (5), or a pharmacologically acceptable salt thereof.

2. A depsipeptide derivative of claim 1 containing a piperazinone ring represented by formula (1')

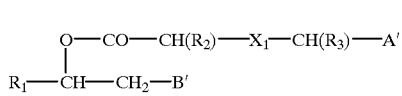

(1')

wherein
$X_1$ represents $N(R_4)$—CO, $N(R_5)$—$CH_2$, $CH_2$—CO, $CH_2$—$CH_2$, CH=CH, $CH_2$—CH(OH) or CH(OH)—CH(OH), $R_1$ represents a $C_5$–$C_{20}$ alkyl group or a $C_5$–$C_{15}$ alkoxy $C_1$–$C_4$ alkyl group, $R_2$–$R_5$ represent a hydrogen atom or a $C_1$–$C_6$ alkyl group, A' represents a group of formula (2)

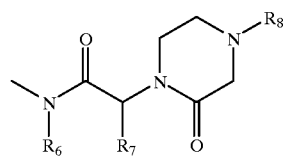

(2)

wherein $R_6$ represents a hydrogen atom or a $C_1$–$C_6$ alkyl group, $R_7$ represents $(CH_2)_{m1}$—COOH wherein $m_1$ represents an integer of 1–3 or $(CH_2)_{n1}$—$CONH_2$ wherein $n_1$ represents 2 or 3, and $R_8$ represents a hydrogen atom or an amine-protecting group, and B' represents a carboxyl group or a $C_1$–$C_6$ alkoxycarbonyl group, provided that the carboxyl group in the above-mentioned A' and B' may protected by a protecting group, or a pharmacologically acceptable salt thereof.

3. A depsipeptide derivative of claim 1 containing a piperazinone ring represented by formula (1")

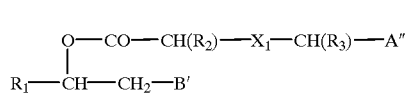

(1")

wherein
$X_1$ represents $N(R_4)$—CO, $N(R_5)$—$CH_2$, $CH_2$—CO, $CH_2$—$CH_2$, CH=CH, $CH_2$—CH(OH) or CH(OH)—CH(OH), $R_1$ represents a $C_5$–$C_{20}$ alkyl group or a $C_5$–$C_{15}$ alkoxy $C_1$–$C_4$ alkyl group, $R_2$–$R_5$ represent a hydrogen atom or a $C_1$–$C_6$ alkyl group, A" represents a group of formula (3)

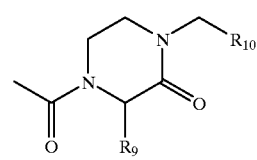

(3)

wherein $R_9$ represents $(CH_2)_{m1}$—COOH wherein $m_1$ represents an integer of 1–3 or $(CH_2)_{n1}$—$CONH_2$ wherein n, represents 2 or 3, and $R_{10}$ represents a hydrogen atom, a $C_1$–$C_6$ alkyl group, a carboxyl group or a $C_1$–$C_6$ alkoxycarbonyl group, and B' represents a carboxyl group or a $C_1$–$C_6$ alkoxycarbonyl group, provided that the carboxyl group in the above-mentioned A" and B' may be protected by an protecting group, or a pharmaceutically acceptable salt thereof.

4. A medicine which comprises as an active ingredient a depsipeptide derivative containing a piperazinone ring or a pharmacologically acceptable salt thereof as defined in claim 1.

5. A medicine of claim 4 wherein the medicine is an accelerator for the production of apolipoprotein E.

6. A medicine of claim 4 wherein the medicine is an agent for the treatment of neurologic injury.

7. A medicine of claim 4 wherein the medicine is an agent for the treatment of dementia.

8. A medicine of claim 4 wherein the medicine is an antihyperlipidemic agent.

* * * * *

UNITED STATES PATENT AND TRADEMARK OFFICE
CERTIFICATE OF CORRECTION

PATENT NO. : 6,288,038 B1
DATED : September 11, 2001
INVENTOR(S) : Makoto Yanai et al.

It is certified that error appears in the above-identified patent and that said Letters Patent is hereby corrected as shown below:

<u>Claim 2,</u>
Line 33, after "may", insert -- be --;

<u>Claim 3,</u>
Line 16, at the end of the line, change "n," to -- $n_1$ --.

Signed and Sealed this

Twenty-sixth Day of February, 2002

Attest:

JAMES E. ROGAN
Attesting Officer
Director of the United States Patent and Trademark Office